United States Patent [19]

Peuckert et al.

[11] 4,378,232
[45] Mar. 29, 1983

[54] METHOD FOR PRODUCTION OF ACETYLENE

[75] Inventors: Cornelius Peuckert, Dinslaken; Herbert Baumann, Essen; Dirk Bittner, Essen; Jürgen Klein, Essen; Harald Jüntgen, Essen, all of Fed. Rep. of Germany

[73] Assignee: Bergwerksverband GmbH, Essen, Fed. Rep. of Germany

[21] Appl. No.: 218,281

[22] Filed: Dec. 18, 1980

[30] Foreign Application Priority Data

Dec. 28, 1979 [DE] Fed. Rep. of Germany ....... 2952519

[51] Int. Cl.³ .............................................. C10J 3/00
[52] U.S. Cl. ...................................... 48/210; 204/171; 585/539
[58] Field of Search .......................... 48/210, 65, 216; 204/171; 585/539, 538

[56] References Cited

U.S. PATENT DOCUMENTS 4,181,504 1/1980 Camacho ............................. 48/210

OTHER PUBLICATIONS

"Arc-Coal Process Development", R&D Report No. 34, 1972, pp. 3-47.
Chemical Abstracts, vol. 93, 1980, No. 117002p.

*Primary Examiner*—S. Leon Bashore, Jr.
*Assistant Examiner*—Michael Goldman
*Attorney, Agent, or Firm*—Michael J. Striker

[57] ABSTRACT

A method for the production of acetylene from coal and hydrogen is provided by electric arc heating. The coal has a content of volatile components (i.waf) from about 25 to 44 percent and a content of organic oxygen (i.waf) of less than 9 percent and is ground to a diameter of less than 0.5 mm. The coal is then separated into two to four grain size fractions and one of the grain size fractions is loaded on a hydrogen containing gas. The gas carrying the coal is heated by way of an electric arc with an energy of from about 5 to 20 kJ/l (in normal state). The ratio of electric power employed to coal stream is from about 4,000 to 40,000 kJ/kg coal. The coal is heated for a time duration about inversely proportional to the third root of the specific outer surface of the coal gain fraction. The resulting product gas is quenched with cold liquid hydrocarbons, with hydrogen or water. Acetylene yields of up to about 0.41 kg acetylene per kg coal can be obtained.

10 Claims, 1 Drawing Figure

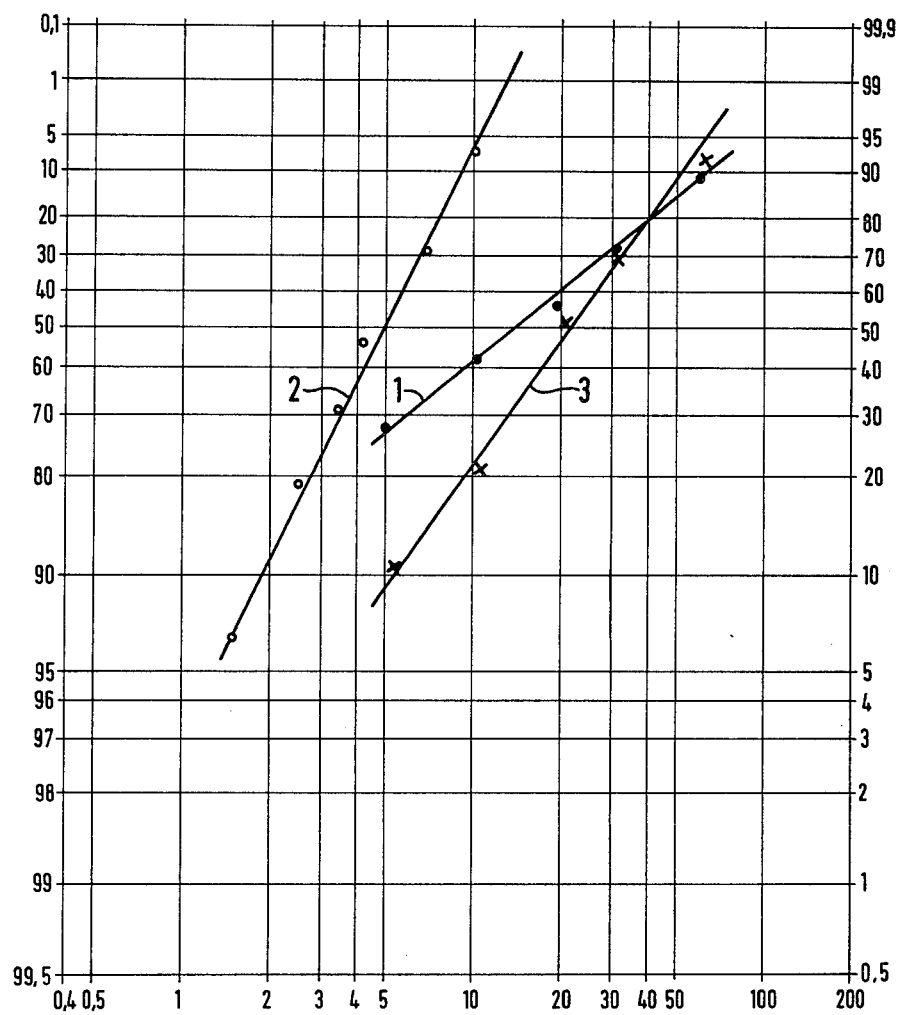

METHOD FOR PRODUCTION OF ACETYLENE

DESCRIPTION

BACKGROUND OF THE INVENTION

1. Field of the Invention

The present invention relates to a process for producing acetylene employing coal reduced in an electric arc.

2. Brief Description of the Background of the Invention Including Prior Art

Acetylene is generated from other hydrocarbons at temperatures above about 1,400° C. Since acetylene is unstable it would in the absence of preventive measures decompose within a short time up to the equilibrium concentration, which is very low at 1,400° C. and which becomes even lower at lower temperatures. Therefor, the temperature has to be suddenly dropped or quenched at that temperature, where the acetylene concentration is highest in order to freeze in the state of high acetylene concentration. Such sudden temperature drop can be achieved by feeding in water through a nozzle, by gaseous, liquid or solid hydrocarbons, by recirculated products or in other ways.

To obtain the high temperatures required for the formation of acetylene an electric arc discharge can be employed. The reaction process in a reactor employing an electric arc is different for all raw materials.

It is known to produce acetylene from gaseous or liquid hydrocarbons such as methane or mineral oil (Ullmanns Enzyklopaedie der technischen Chemie, 4th edition (1974) Volume 7, pages 47 to 49).

It is also known to produce acetylene from bituminous coals with a content in volatile components (i.waf) of more than about 38 weight percent in an electric arc reactor where however the acetylene yield was only about 7 to 9 weight percent (P. H. Given, Reposrt to Office of Coal Research, U.S. State Department of Interior, Report No. 61, Interim Report No. 5, pages 4 and 5).

SUMMARY OF THE INVENTION

1. Purposes of the Invention

It is an object of the invention to produce acetylene in an electric arc reactor from coal with high yield and at a specific energy requirement as low as possible.

It is another object of the invention to provide coals useful in the production of acetylene.

It is a further object of the invention to look for relationships and conditions allowing the efficient employment of coal in the electric arc production of acetylene.

These and other objects and advantages of the present invention will become evident from the description which follow.

2. Brief Description of the Invention

The present invention provides a method for the production of acetylene which comprises grinding coal to less than 0.5 mm diameter, where the coal has a content of volatile components (i.waf) from about 25 to 44 percent and a content of organic oxygen (i.waf) of less than 9 percent, separating the coal into at least two grain size fractions, loading a hydrogen containing gas with one of the grain size fractions of coal, heating the gas carrying the coal through an electric arc with an energy of from about 5 to 20 KJ/l (in normal state) and where the ratio of electric power to coal stream is from about 4,000 to 40,000 KJ/kg coal for a time duration about inversely proportional to the third root of the specific outer surface of the coal grain fraction, and quenching the resulting product gas with cold liquid hydrocarbons or water. Preferably the contents of volatile components in the coal is from about 30 to 40 percent and the oxygen content (i.waf) is preferably less than about 5 percent. The coal employed can be lignite, subbituminous to bituminous coal and anthracite.

Preferably the specific outer surface of the coal ground to less than 0.5 mm is according to the Blaine method from about 0.5 to 2.0 $m^2/cm^3$. It is preferred to have in the grain size fraction distribution of the coal fraction employed the medium slope of the grain characteristic line amounting to from about 1.2 to 2.5 in the Rosin-Rammler-Sperling-Bennet-grid between passages of 10 to 80 percent.

The invention accordingly consists in the series of steps which will be exemplified in the method and process hereinafter described and of which the scope of application will be indicated in the appended claims.

BRIEF DESCRIPTION OF THE DRAWING

In the accompanying drawing is shown in FIG. 1 a diagram showing the dependence of the grain size d on the residue R in percent in a Rosin-Rammler-Sperling-Bennet-grid.

DESCRIPTION OF INVENTION AND PREFERRED EMBODIMENTS

In accordance with the present invention coal is ground to a diameter of less than 0.5 mm, which has a content of volatile components (i.waf) of from about 25 to 44 percent and preferably from 30 to 40 percent and a content of organic oxygen of less than about 9 percent. The coal is advantageously separated into two to four grain size fractions and each of these grain fractions is fed to a special electric arc reactor and has there a dwell time about inversely proportional to the third root of the specific outer surface of the individual coal fractions and is then quenched.

In the operation of the electric arc d.c current or a.c current (two or three phase) can be employed about equally. The ratio of current to voltage depends on the length of the arc and is fixed by the reactor geometry and by the mode of operation, for example with or without gas recirculation. For the production of acetylene processes employing a current/voltage ratio larger than 1 or employing a current/voltage ratio smaller than 1 can be used. For the stabilization of the electric arc for example a gas turbulence can be employed (Proc. 8th World Petroleum Congress (1971) Vol 4, Pages 379–388) or a magnetic field can be employed, which puts the arc in rotation (U.S. Pat. No. 3,073 769).

In the reaction in the electric arc reactor the formation of the acetylene competes with its decomposition such that in the course of time of the reaction process a maximum is generated of the concentration of the acetylene and of the radicals forming acetylene upon quenching. It is necessary independent of the type of coal employed for an optimal production of acetylene to quench the products at that place in the reactor where this maximum is reached.

To achieve suitable conditions the gas is heated by the electric arc to an energy of from about 5 to 20 kJ/1 (in normal state) and as much coal is fed to the reactor that the ratio of the electric power to the coal stream is from about 4,000 to 40,000 kJ per kg of coal. It is advantageous, when the gas, which is fed into the reactor, contains a large part in hydrogen. The substantial reason for this is that hydrogen impedes the decomposition of acetylene.

The economic viability of a process for making acetylene from coal depends substantially on the yield in acetylene, the concentration of the acetylene in the product gas and the specific energy requirements (energy requirements for the production of 1 kg acetylene): The acetylene yield and the acetylene concentration should be as high as possible and the specific energy requirement should be as low as possible.

It was found that the acetylene yield increases when the pyrolysis of the coal is more rapidly terminated, since in a rapid pyrolysis at the end of the pyrolysis less of the initially formed acetylene is decomposed compared to a slow pyrolysis. In accordance with the present invention the pyrolysis time can be shortened by two different measures; either coal is employed having a very small average grain diameter and the specific surface of which is very high, respectively, in fact up to about 1.54 m$^2$/cm$^3$ as measured with the Blaine method or it is provided that with coarser grains the width of the grain size distribution is very narrow, for example the uniformity parameter n of a Rosin-Rammler-Sperling-Bennet-distribution (RRSB-distribution) (Ullmans Enzyklopaedie der technischen Chemie, 4th edition, Volume 2, page 27) should be from about 1.2 to 2.5.

Thus in accordance with the present invention the specific outer surface of the coal should be from about 0.5 to 2.0 m$^2$/cm$^3$. It is determined for example with the Blaine method (DIN 66 127, ASTM C204-68).

In addition according to the present invention in the grain size distribution of each coal fraction the medium slope of the grain characteristic line in the Rosin-Rammler-Sperling-Bennet-grid should be at least 1.2 between the passages of 10 to 80 percent.

All coals from lignites, brown coals via variously high coalificated mineral coals to anthracite are suitable as starting materials for the production of acetylene. The yield of acetylene however depends on the coalification of the coal. In the present invention the content of the coal in organic oxygen is just as important as the content in volatile components. The oxygen content of the coals reacts in the electric arc reactor with a part of the volatile carbon to carbon monoxide, such that this carbon is not available for the formation of acetylene. In lignites having a higher content in organic bound oxygen the yield of acetylene is lower for this reason compared with high volatile mineral coals, although the lignites have a higher content in volatile components.

The process according to the present invention is then particularly advantageous when ground coal having in general a broad grain size distribution is separated by suitable steps such as for example by air classification into several grain fractions with narrower grain size distributions and each of these grain fractions can be reacted in a separate electric arc reactor wherein the dwell time of the coal in the hot reaction zone is adapted to the grain size.

EXAMPLES

Mineral coal of a grain size of less than 0.5 mm with a content of volatile components (i.waf) of 38.6 weight percent and a content in organic oxygen (i.waf) of 8.2 weight percent is entered in three different grain size distributions into a reactor for the generation of acetylene from coal, wherein a mixture of hydrogen and argon is heated by an electric arc burning between a rod shaped cathode and an anode formed as a hollow cylinder. The anode is water-cooled. The electric arc is placed into rotation by a magnetic coil. The power of the electric arc, less the power loss removed with the cooling water amounts to 19.7 kW. Into the hot hydrogen argon mixture a hydrogen stream carrying 84 g/min coal is jetted in. The total amount of gas stream fed into the reaction space is 156 l$_n$/min comprising 91 volume percent hydrogen and 9 volume percent argon. The coal is reacted to acetylene in the reactor space. The reaction products are quenched with a hydrogen quench.

EXAMPLE 1

The grain size of the starting coal is characterized by 90 weight percent smaller than 65 μm, 50 weight percent less than 13 μm and a uniformity parameter n of the RRSB distribution of 0.8 (Curve 1, FIG. 1) The Baine surface is 1.26 m$^2$cm$^3$. The dwell time of the coal in the reaction volume until quenching is $2.8 \cdot 10^{-3}$ sec.

A yield of acetylene is obtained amounting to 0.30 kg acetylene per kg of coal. A specific energy requirement (without the energy losses in the cooling water) of 13 kWh/kg acetylene can be calculated from this.

EXAMPLE 2

The starting coal of example 1 is separated by air classification into a fine and a coarse grain fraction and 39.7 weight percent of the starting coal employed fall into the fraction of the fine grain. 90 weight percent of the fine grain fraction are smaller than 9 μm and 50 weight percent are smaller than 4.8 μm, the uniformity parameter n of the RRSB distribution is 2.0 (Curve 2, FIG. 1) and the Blaine surface of the fine grain fraction is 2.30 m$^2$/cm$^3$. The dwell time for the fine grain fraction in the reaction volume amounts to $2.3 \cdot 10^{-3}$ sec. This dwell time is calculated from the dwell time of the grain distribution employed in example 1 and from the ratio of the Blaine surface of the starting coal to the fine fraction according to the formula: Dwell time of the fine grain fraction $= 2.8 \cdot \sqrt[3]{1.26/2.30}$ ms. An acetylene yield of 0.41 kg of acetylene per kg coal is obtained for the fine grain fraction. A specific energy requirement (without the loss energy carried with the cooling water) is calculated to 9.5 kWh/kg acetylene. The higher acetylene yield and the lower specific energy requirement when compared with example 1 can be explained with the higher Blaine surface and the narrower grain size distribution, which shows up in the larger uniformity parameter n of the RRSB distribution.

EXAMPLE 3

60.3 weight percent of the starting coal employed fall into the coarse grain fraction produced by the air classification. 90 weight percent of the coarse grain fraction are smaller than 50 μm and 50 weight percent are smaller than 22 μm, the uniformity parameter of the RRSB distribution is 1.4 (Curve 3, FIG. 1) and the Blaine surface is 0.47 m$^2$/cm$^3$. The dwell time for the coarse grain fraction in the reaction volume is $3.9 \cdot 10^{-3}$ sec; this dwell time is calculated from the dwell time of the grain distribution employed in example 1 and from the ratio of the Blaine surfaces of the starting coal to the coarse graine fraction according to the formula: Dwell time of the coarse grain fraction $= 2.8 \cdot \sqrt[3]{1.26/0.47}$ ms. An acetylene yield of 0.28 kg acetylene per kg coal is obtained for the coarse grain fraction. A specific energy requirement (without the energy loss amount in the cooling water) of 14.0 kWh/kg acetylene is calculated from this. The lower acetylene yield and the higher specific energy requirement when compared with examples 1 and 2 can be explained with the smaller Blaine surface. This effect was not compensated by the narrower grain size distribution when compared with example 1, which narrower distribution is expressed in the larger uniformity parameter n of the RRSB distribution.

When calculating from the examples 2 and 3 the acetylene yield and the specific energy requirement for the total of the two grain fractions under consideration of the respective amounts, then one obtains an acetylene yield of 0.33 kg acetylene per kg coal and a specific energy requirement of 11.8 kWh/kg acetylene. Compared with the yield and the specific energy requirement of the non fractionated coal in example 1 this result means an advantage, which is achieved by the narrower distributions (larger n-values) of the fine and coarse fractions.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is:

1. A method for the production of acetylene comprising:
   grinding coal to less than 0.5 mm diameter, where the coal has a content of volatile components from about 25 to 44 percent and a content of organic oxygen of less than 9 percent;
   separating the coal into at least two grain size fractions; loading hydrogen containing gas with said grain size fractions of coal; feeding each of said grain size fractions which have been loaded into hydrogen containing gas to separate electric arc rectors; heating said grain size fractions, which have been loaded into hydrogen containing gas, in each of said reactors through an electric arc with an energy of from about 5 to 20 kJ/l and where the ratio of electric power to coal stream is from about 4,000 to 40,000 kJ/kg coal for a time duration about inversely proportional to the third root of the specific outer surface of the coal grain fraction; and quenching the resulting product gas with cold liquid hydrocarbons or water.

2. The method according to claim 1, wherein the content of volatile components is from about 30 to 40 percent.

3. The method according to claim 1, wherein the coal is bituminous coal.

4. The method according to claim 1, wherein the coal is subbituminous coal.

5. The method according to claim 1, wherein the specific outer surface of the coal ground to less than 0.5 mm is according to the Blaine method from about 0.5 to 2.0 $m^2/cm^3$.

6. The method according to claim 1, wherein in the grain size fraction distribution of the coal fraction employed, the medium slope of the grain charcteristic line amounts to from about 1.2 to 2.5 in the Rosin-Rammler-Sperling-Bennet-grid between passages of 10 to 80 percent.

7. In a process for the production of acetylene by direct transformation of brown or mineral coal in a gas containing hydrogen comprising the steps of: loading the gas containing hydrogen with such an amount of coal that the ratio of electric power to coal stream is from about 4,000 to 40,000 kJ/kg coal, heating the gas containing hydrogen and coal by an electric arc with an energy of from about 5 to 20KJ/l, and quenching the resulting product gas with cold liquid hydrocarbons, cold gas or water, the improvement comprising grinding the coal to less than 0.5 mm diameter, said coal having a content of volatile components of from about 25 to 44 percent and a content of organic oxygen of under 9 percent, separating the coal into from about 2 to 4 different coal grain size fractions, supplying each of these coal grain size fractions to a separate electric arc reactor, quenching the product gas after a dwell time in the hot gas, which dwell time is about inversely proportional to the third root of the specific outer surface of the individual coal fraction.

8. The process according to claim 7, wherein the content of volatile components is from about 30 to 40 percent.

9. The process according to claim 7, wherein the specific outer surface of the coal ground to less than 0.5 mm is according to the Blaine method from about 0.5 to 2.0 $m^2/m^3$.

10. The process according to claim 7, wherein in the grain size fraction distribution of the coal fraction employed, the medium slope of the grain characteristic line amounts to from about 1.2 to 2.5 in the Rosin-Rammler-Sperling-Bennet-grid between passages of 10 to 80 percent.

* * * * *